(12) United States Patent
Prausnitz et al.

(10) Patent No.: US 7,226,439 B2
(45) Date of Patent: Jun. 5, 2007

(54) MICRONEEDLE DRUG DELIVERY DEVICE

(75) Inventors: Mark R. Prausnitz, Decatur, GA (US);
Mark G. Allen, Atlanta, GA (US);
Inder-Jeet Gujral, Cambridge, MA (US)

(73) Assignee: Georgia Tech Research Corporation, Atlanta, GA (US)

( * ) Notice: Subject to any disclaimer, the term of this patent is extended or adjusted under 35 U.S.C. 154(b) by 344 days.

(21) Appl. No.: 10/454,973

(22) Filed: Jun. 4, 2003

(65) Prior Publication Data
US 2003/0208167 A1 Nov. 6, 2003

Related U.S. Application Data

(63) Continuation of application No. 09/452,979, filed on Dec. 2, 1999, now Pat. No. 6,611,707.

(60) Provisional application No. 60/137,621, filed on Jun. 4, 1999.

(51) Int. Cl.
*A61M 31/00* (2006.01)
(52) U.S. Cl. .................................... 604/506
(58) Field of Classification Search ................ 424/424, 424/449; 604/191, 186, 20, 22, 35, 46, 181, 604/183, 239, 261, 272, 890.1
See application file for complete search history.

(56) References Cited

U.S. PATENT DOCUMENTS

| | | | |
|---|---|---|---|
| 2,893,392 A | 7/1959 | Wagner et al. | |
| 3,034,507 A | 5/1962 | McConnell et al. | |
| 3,086,530 A | 4/1963 | Groom | |
| 3,123,212 A | 3/1964 | Taylor et al. | |
| 3,136,314 A | 6/1964 | Kravitz | |
| RE25,637 E | 9/1964 | Kravitz et al. | |

(Continued)

FOREIGN PATENT DOCUMENTS

DE 195 25 607 1/1997

(Continued)

OTHER PUBLICATIONS

Abrams, S.B. Versatile biosensor is compact and cheap. Biophotonics International 32-34 (Jan./Feb. 1998).

(Continued)

*Primary Examiner*—Manuel Mendez
(74) *Attorney, Agent, or Firm*—Fish & Neave IP Group Ropes & Gray LLP

(57) ABSTRACT

Simple microneedle devices for delivery of drugs across or into biological tissue are provided, which permit drug delivery at clinically relevant rates across or into skin or other tissue barriers, with minimal or no damage, pain, or irritation to the tissue. The devices include a substrate to which a plurality of hollow microneedles are attached or integrated, and at least one reservoir, containing the drug, selectably in communication with the microneedles, wherein the volume or amount of drug to be delivered can be selectively altered. The reservoir can be formed of a deformable, preferably elastic, material. The device typically includes a means, such as a plunger, for compressing the reservoir to drive the drug from the reservoir through the microneedles. In one embodiment, the reservoir is a syringe or pump connected to the substrate.

18 Claims, 4 Drawing Sheets

U.S. PATENT DOCUMENTS

| | | | |
|---|---|---|---|
| 3,221,739 | A | 12/1965 | Rosenthal |
| 3,221,740 | A | 12/1965 | Rosenthal |
| 3,556,080 | A | 1/1971 | Hein |
| 3,596,660 | A | 8/1971 | Melone |
| 3,675,766 | A | 7/1972 | Rosenthal |
| 3,918,449 | A | 11/1975 | Pistor |
| 3,964,482 | A | 6/1976 | Gerstel et al. |
| 4,109,655 | A | 8/1978 | Chacornac |
| 4,159,659 | A | 7/1979 | Nightingale |
| 4,222,392 | A | 9/1980 | Brennan |
| 4,320,758 | A | 3/1982 | Eckenhoff et al. |
| 4,664,651 | A | 5/1987 | Weinshenker et al. |
| 4,671,288 | A | 6/1987 | Gough |
| 4,703,761 | A | 11/1987 | Rathbone et al. |
| 4,771,660 | A | 9/1988 | Yacowitz |
| 4,775,361 | A | 10/1988 | Jacques et al. |
| 4,798,582 | A | 1/1989 | Sarath et al. |
| 4,921,475 | A | 5/1990 | Sibalis |
| 4,969,468 | A | 11/1990 | Byers et al. |
| 5,035,711 | A | 7/1991 | Aoki et al. |
| 5,054,339 | A | 10/1991 | Yacowitz |
| 5,138,220 | A | 8/1992 | Kirkpatrick |
| 5,147,355 | A | 9/1992 | Friedman et al. |
| 5,250,023 | A | 10/1993 | Lee et al. |
| 5,279,544 | A | 1/1994 | Gross et al. |
| 5,279,552 | A | 1/1994 | Magnet |
| 5,335,670 | A | 8/1994 | Fishman |
| 5,364,374 | A | 11/1994 | Morrison et al. |
| 5,383,512 | A | 1/1995 | Jarvis |
| 5,401,242 | A | 3/1995 | Yacowitz |
| 5,457,041 | A | 10/1995 | Ginaven et al. |
| 5,527,288 | A | 6/1996 | Gross et al. |
| 5,582,184 | A | 12/1996 | Erickson et al. |
| 5,591,139 | A | 1/1997 | Lin et al. |
| 5,599,302 | A | 2/1997 | Lilley et al. |
| 5,605,662 | A | 2/1997 | Heller et al. |
| 5,611,806 | A | 3/1997 | Jang |
| 5,611,809 | A | 3/1997 | Marshall et al. |
| 5,611,942 | A | 3/1997 | Mitsui et al. |
| 5,618,295 | A | 4/1997 | Min |
| 5,632,957 | A | 5/1997 | Heller et al. |
| 5,658,515 | A | 8/1997 | Lee et al. |
| 5,697,901 | A | 12/1997 | Eriksson |
| 5,758,505 | A | 6/1998 | Dobak et al. |
| 5,801,057 | A | 9/1998 | Smart et al. |
| 5,807,375 | A | 9/1998 | Gross et al. |
| 5,843,114 | A | 12/1998 | Jang |
| 5,848,991 | A | 12/1998 | Gross et al. |
| 5,852,495 | A | 12/1998 | Parce |
| 5,855,801 | A | 1/1999 | Lin et al. |
| 5,858,188 | A | 1/1999 | Soane et al. |
| 5,865,786 | A | 2/1999 | Sibalis et al. |
| 5,865,796 | A | 2/1999 | McCabe |
| 5,876,675 | A | 3/1999 | Kennedy |
| 5,879,326 | A | 3/1999 | Godshall et al. |
| 5,883,211 | A | 3/1999 | Sassi et al. |
| 5,885,211 | A | 3/1999 | Eppstein et al. |
| 5,899,880 | A | 5/1999 | Bellhouse et al. |
| 5,911,223 | A | 6/1999 | Weaver |
| 5,919,159 | A | 7/1999 | Lilley et al. |
| 6,050,988 | A | 4/2000 | Zuck |
| 6,080,116 | A | 6/2000 | Erickson et al. |
| 6,132,755 | A | 10/2000 | Eicher et al. |
| 6,312,612 | B1 | 11/2001 | Feisal et al. |
| 6,334,856 | B1 | 1/2002 | Allen et al. |
| 6,503,231 | B1 | 1/2003 | Prausnitz et al. |
| 6,611,707 | B1* | 8/2003 | Prausnitz et al. ............ 604/21 |

2001/0053891 A1   12/2001   Ackley

FOREIGN PATENT DOCUMENTS

| | | |
|---|---|---|
| EP | 0497620 | 8/1992 |
| EP | 0652600 A1 | 5/1995 |
| JP | 7-132119 | 5/1995 |
| JP | 7-196314 | 8/1995 |
| WO | WO 93/17754 A1 | 9/1993 |
| WO | WO 96/37256 A1 | 11/1996 |
| WO | WO 96/40365 A1 | 12/1996 |
| WO | WO 96/41236 A1 | 12/1996 |
| WO | WO 97/07734 A1 | 3/1997 |
| WO | WO 98/00193 A1 | 1/1998 |
| WO | WO 98/00194 | 1/1998 |
| WO | WO 98/28037 A1 | 7/1998 |
| WO | WO 00/48669 | 8/2000 |

OTHER PUBLICATIONS

101 Uses for Tiny Tubules, Science 247 (1990).

Amsden & Goosen, Transdermal Delivery of Peptide and Protein Drugs: an Overview, AIChE Journal 41(8): 1972-97 (1995).

Bronaugh & Mailback, Percutaneous Absorption, Mechanisms-Methodology-Drug Delivery (Marcel Dekker: New York, 1989).

Brumlik & Martin, Template Synthesis of Metal Microtubules, J. Am. Chem. Soc. 113:3174-75 (1991).

Despont, et al., High-Aspect-Ratio, Negative-Tone Near-UV Photoresist for MEMS, Proc. of IEEE 10th Annual International Workshop on MEMS, Nagoya, Japan, pp. 518-22 (Jan. 26-30, 1997).

Chun, K. et al. Fabrication of Array of Hollow Microcapillaries Used for Injection of Genetic Materials into Animal/Plant Cells. Jpn. J. Appl. Phys. 38, 279-281 (1999).

Clarke, M.S.F. and McNeil, P.L. Syringe loading introduces macromolecules into living mammalian cell cytosol. J. Cell. Sci. 102, 533-541 (1992).

Edell, et. al., Factors Influencing the Biocompatibility of Insertable Silicon Microshafts in Cerebral Cortex, IEEE Transactions on Biomedical Engineering 39(6):635-43 (1992).

Eleventh Annual International Workshop on Micro Electro Mechanical Systems, Heidelberg, Germany (Jan. 25-29, 1998). IEEE Catalog No. 98CH36176.

Frazier, et al., Two dimensional metallic microelectrode arrays for extracellular stimulation and recording of neurons, IEEE Proceedings of the Micro Electro Mechanical Systems Conference, pp. 195-200 (1993).

Frazier, et al., Metallic Microstructures Fabricated Using Photosensitive Polyimide Electroplanting Molds, Journal of Microelectromechanical Systems 2:87-97 (1993).

Hadgraft & Guy, eds., Transdermal Drug Delivery: Developmental Issues and Research Initiatives (Marcel Dekker, New York 1989).

Haga, et al., Transdermal iontophoretic delivery of insulin using a photoetched microdevice, J. Controlled Release 43:139-49 (1997).

Hashmi, et al., Genetic Transformation of Nematodes Using Arrays of Micromechanical Piercing Structures, BioTechniques 19(5):766-70 (1995).

Henry, et al., Microfabricated microneedles: A novel method to increase transdermal drug delivery, J. Pharm. Sci. 87:922-25 (1998).

Henry, et al., Micromachined Needles for the Transdermal Delivery of Drugs, Micro Electro Mechanical Systems, Heidleberg, Germany, pp. 494-498 (Jan. 26-29, 1998).

Hoffert, Transcutaneous methods get under the skin, The Scientist 12 (1998).

Infiltrator Intramural Drug Delivery: A New Generation of Drug Delivery Catheters from InterVentional Technologies, Inc., San Diego, CA (1997).

Jaeger, Introduction to Microelectronic Fabrication (Addison-Wesley Publishing Co., Reading MA 1988).

Jansen, et al., The Black Silicon Method IV: The Fabrication of Three-Dimensional Structures in Silicon with High Aspect Ratios for Scanning Probe Microscopy and Other Applications, IEEE Proceedings of Micro Electro Mechanical Systems Conference, pp. 88-93 (1995).

Laemer, et al., Bosch Deep Silicon Etching: Improving Uniformity and Etch Rate for Advanced MEMS Applications, Micro Electro Mechanical Systems, Orlando, FL, USA (Jan. 17-21, 1999).

Langer, Drug Delivery and Targeting, Nature 392:5-10 (1998).

Lehmann, Porous Silicon—A New Material for MEMS, IEEE Proceedings of the Micro Electro Mechanical Systems Conference, pp. 1-6 (1996).

Lin, et al., Silicon Processed Microneedles, The 7th International Conference on Solid-State Sensors and Actuators 237-40 (1993).

Martin, et al., Template Synthesis of Organic Microtubules, J. Am. Chem. Soc. 112:8976-77 (1990).

Najafi, et al., Strength Characterization of Silicon Microprobes in Neurophysiological Tissues, IEEE Transcriptions on Biomedical Engineering 37(5):474-81 (1990).

Prausnitz, Reversible Skin Permeabilization for Transdermal Delivery of Macromolecules, Critical Reviews in Therapeutic Drug Carrier Systems 37(5):474-81 (100).

Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, WA 1997).

Quan, Plasma etch yields microneedle arrays, Electronic Engineering Times 63:63-64 (1998).

Reiss, Glucose- and Blood-Monitoring Systems Vie for Top Spot, Biophotonics Int'l, pp. 43-45 (1997).

Runyan & Bean, Semiconductor Integrated Circuit Processing Technology, Addison-Wesley Publishing Co.: Reading, MA 1990.

Schift, et al., Fabrication of replicated high precision insert elements for micro-optical bench arrangements, Proc. SPIE—International Soc. Optical Engineer 3513:122-34 (1998).

Single-crystal whiskers, Biophotonics Int'l p. 64 (Nov./Dec. 1996).

Talbot & Pisano, Polymolding: Two Wafer Polysilicon Micromolding of Closed-Flow Passages for Microneedles and Microfluidic Devices, Solid-State Sensor and Actuator Workshop, Hilton Head Island, South Carolina, Jun. 8-11 266-68 (1988).

Trimmer, et al., Injection of DNA into Plant and Animal Tissues with Micromechanical Piercing Structures, IEEE Proceedings of Micro Mechanical Systems Conference, pp. 111-115 (1995).

Weber, et al., Micromolding—a powerful tool for the large scale production of precise microstructures, Proc. SPIE-International Soc. Optical Engineer 2879:156-167 (1996).

Zuska, Microtechnology Opens Doors to the Universe of Small Space, Medical Device and Diagnostic Industry, p. 131 (1997).

* cited by examiner

MICRONEEDLE DRUG DELIVERY DEVICE

CROSS-REFERENCE TO RELATED APPLICATIONS

This application is a continuation of U.S. Ser. No. 09/452,979, now U.S. Pat. No. 6,611,707, filed Dec. 2, 1999, which claims priority to U.S. provisional application Ser. No. 60/137,621, filed Jun. 4, 1999, the specifications of which are incorporated by reference herein in their entireties.

BACKGROUND OF THE INVENTION

A common technique for delivering drugs across or into biological tissue is the use of a needle, such as those used with standard syringes or catheters, to transport drugs across (through) the skin. While effective for this purpose, needles generally cause pain; local damage to the skin at the site of insertion; bleeding, which increases the risk of disease transmission; and a wound sufficiently large to be a site of infection. Needle techniques also generally require administration by one trained in its use. The needle technique also is undesirable for long term, controlled continuous drug delivery.

An alternative delivery technique is the transdermal patch, which usually relies on diffusion of the drug across the skin. However, this method is not useful for many drugs, due to the poor permeability (i.e. effective barrier properties) of the skin. The rate of diffusion depends in part on the size and hydrophilicity of the drug molecules and the concentration gradient across the stratum corneum. Few drugs have the necessary physiochemical properties to be effectively delivered through the skin by passive diffusion. Iontophoresis, electroporation, ultrasound, and heat (so-called active systems) have been used in an attempt to improve the rate of delivery. While providing varying degrees of enhancement, these techniques are not suitable for all types of drugs, failing to provide the desired level of delivery. In some cases, they are also painful and inconvenient or impractical for continuous controlled drug delivery over a period of hours or days.

Attempts have been made to design alternative devices for active transfer of drugs, but there remains a need for better drug delivery devices, which make smaller incisions, deliver drug with greater efficiency (greater drug delivery per quantity applied) and less variability of drug administration, and/or are easier to use.

It is therefore an object of the present invention to provide a microneedle device for relatively painless, controlled, safe, convenient transdermal delivery of a variety of drugs.

SUMMARY OF THE INVENTION

Simple microneedle devices are provided for delivery of drugs across or into biological tissue, particularly the skin. The microneedle devices permit drug delivery at clinically relevant rates across or into skin or other tissue barriers, with minimal or no damage, pain, or irritation to the tissue.

The devices include a plurality of hollow microneedles, which are attached to or integrated into a substrate, and at least one reservoir selectably in communication with the microneedles, wherein the volume or amount of drug to be delivered can be selectively altered. The reservoir contains the drug to be delivered. In one embodiment, the reservoir is formed of a deformable, preferably elastic, material.

The device also can include means for compressing the reservoir to drive the drug from the reservoir through the microneedles. The means can include a plunger or osmotic pump. In one embodiment, the reservoir is a syringe or pump connected to the substrate.

The device also can include a sealing mechanism to contain the drug in one or more of the reservoirs until it is ready to be delivered or mixed with a liquid carrier. In one embodiment, the sealing mechanism is a fracturable barrier interposed between the reservoir and the substrate.

In one embodiment, the device includes a means for providing feedback to the user to indicate that delivery has been initiated and/or completed. An example of the feedback means is a color change.

In another embodiment, the microneedle device further includes a rate control means, such as a semi-permeable membrane, to regulate the rate or extent of drug which flows through the microneedles.

The microneedle devices preferably are provided with means for preventing undesired reuse of or contact with the microneedles. These means can include protective packaging, such as a peelable liner that temporarily covers the tips of the microneedles. The packaging also can be used to shear off the microneedles following their intended use, thereby preventing their reuse.

DETAILED DESCRIPTION OF THE INVENTION

Figure 1A:
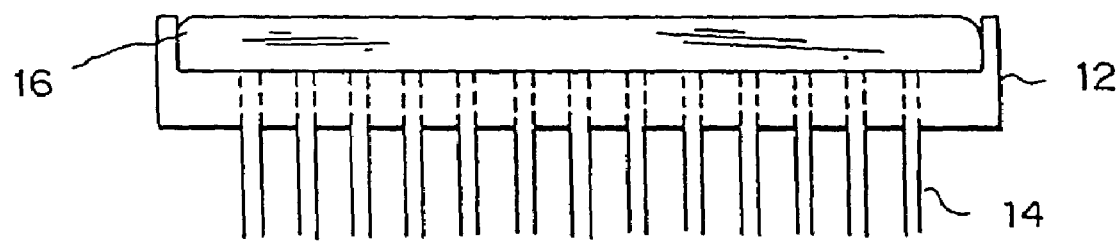
FIGS. 1a–c are cross-sectional views of preferred embodiments of a microneedle drug delivery device. The device of FIG. 1a includes a reservoir and is suitable for transdermal drug delivery. The device of FIGS. 1a and 1b includes a deformable reservoir, wherein delivery is activated by manual, e.g., finger or thumb, pressure applied to compress the reservoir directly (1b) or indirectly (1c).

The microneedle devices include at least three components: at least one, more preferably more, microneedle(s); a substrate to which the base of the microneedle(s) are secured or integrated; and at least one reservoir that is selectably in fluid connection with one or more of the microneedles. Preferably, the microneedles are provided as a multi-dimensional array, in contrast to a device with a single microneedle or single row of microneedles. The microneedle device can be adapted to be a single-use, disposable device, or can be adapted to be fully or partially reusable.

Microneedles

The microneedles are hollow; that is, each contains at least one substantially annular bore or channel having a diameter large enough to permit passage of a drug-containing fluid and/or solid materials through the microneedle. The hollow shafts may be linear, i.e. extend upwardly from needle base to needle tip, or they may take a more complex path, e.g. extend upwardly from the needle base, but then lead to one or more 'portholes' or 'slits' on the sides of the needles, rather than an opening at the needle tip.

The microneedles can be constructed from a variety of materials, including metals, ceramics, semiconductors, organics, polymers, and composites. Preferred materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides.

The microneedles should have the mechanical strength to remain intact while being inserted into the biological barrier, while remaining in place for up to a number of days, and while being removed. In embodiments where the microneedles are formed of biodegradable polymers, the microneedle must to remain intact at least long enough for the microneedle to serve its intended purpose (e.g., its conduit function for delivery of drug). The microneedles should be sterilizable using standard methods such as ethylene oxide or gamma irradiation.

The microneedles can have straight or tapered shafts. In a preferred embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 1 μm and 500 μm, and preferably between 10 and 100 μm. The outer diameter is typically between about 10 μm and about 100 μm, and the inner diameter is typically between about 3 μm and about 80 μm.

In one embodiment the cross-sectional dimensions are designed to leave a residual hole (following microneedle insertion and withdrawal) of less than about 0.2 μm, to avoid making a hole which would allow bacteria to enter the penetration wound. The actual microneedle diameter will typically be in the few micron range, since the holes typically contract following withdrawal of the microneedle. Larger diameter and longer microneedles are acceptable, so long as the microneedle can penetrate the biological barrier to the desired depth.

The length of the microneedles typically is between about 10 μm and 1 mm, preferably between 100 μm and 500 μm, and more preferably between 150 μm and 350 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In transdermal applications, the "insertion depth" of the microneedles is preferably less than about 100–150 μm, so that insertion of the microneedles into the skin does not penetrate into the dermis, thereby avoiding contacting nerves which may cause pain. In such applications, the actual length of the microneedles typically is longer, since the portion of the microneedles distal the tip may not be inserted into the skin; the uninserted length depends on the particular device design and configuration. The actual (overall) height or length of microneedles should be equal to the insertion depth plus the uninserted length.

Substrate

The substrate of the device can be constructed from a variety of materials, including metals, ceramics, semiconductors, organics, polymers, and composites. The substrate includes the base to which the microneedles are attached or integrally formed. The substrate can be adapted to fit a Luer-Lock syringe or other conventionally used drug delivery device that currently uses hypodermic needles as the barrier penetration method.

In one embodiment of the device, the substrate, as well as other components, are formed from flexible materials to allow the device to fit the contours of the biological barrier, such as the skin, vessel walls, or the eye, to which the device is applied. A flexible device may facilitate more consistent penetration of some biological barriers, because penetration can be limited by deviations in the attachment surface. For example, the surface of human skin is not flat due to dermatoglyphics (i.e. tiny wrinkles) and hair. However, for some biological barriers, a rigid substrate may be preferred.

Reservoir

The reservoir is selectably in connection with the microneedle bore, such that the reservoir contents can flow from the reservoir and out through the microneedle tip, into the target tissue. Typically, it is attached to, or integrated into, the substrate, either integrally (as in a one-piece device) or at the moment of drug delivery (as with a Luer-lock type device). The reservoir is to provide suitable, leak-free storage of the drug composition before it is to be delivered. The reservoir should keep the drug composition free of contaminants and degradation-enhancing agents. For example, the reservoir should exclude light when the drug composition contains photo-sensitive materials, and should include an oxygen barrier material in order to minimize exposure of drugs sensitive to oxidation. Also, the reservoir should keep volatile materials inside the reservoir, for example, to prevent water from evaporating, causing the drug composition to dry out and become undeliverable.

The drug reservoir can be substantially rigid or readily deformable. The reservoir can be formed from one or more polymers, metals, ceramics, or combinations thereof. In a preferred embodiment, the reservoir includes a volume surrounded by one or more walls, or includes a porous material, such as a sponge, which can retain, for example, the drug liquid until the material is compressed.

In a preferred embodiment, the reservoir is formed of an elastic material, such as an elastomeric polymer or rubber.

For example, the reservoir can be a balloon-like pouch that is stretched (in tension) when filled with a fluid drug composition to be delivered.

Figure 4A:
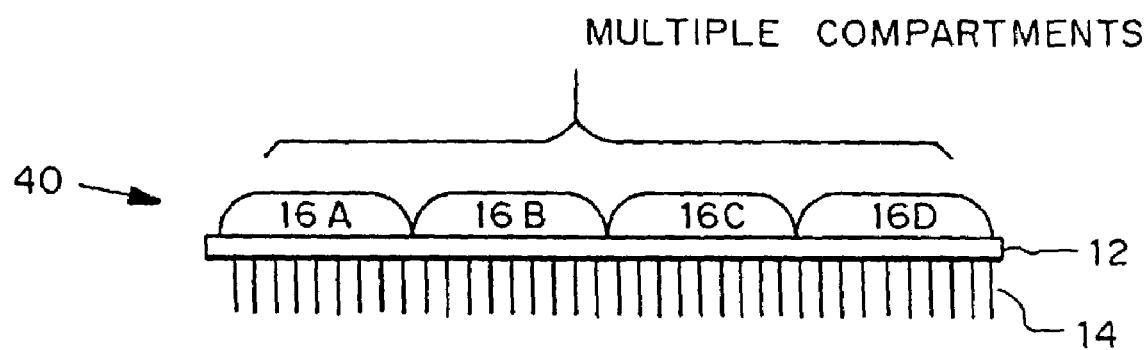
FIGS. 4a–b are cross-sectional views of preferred embodiments of a microneedle drug delivery device having a multiple chambered reservoirs.
Figure 4B:
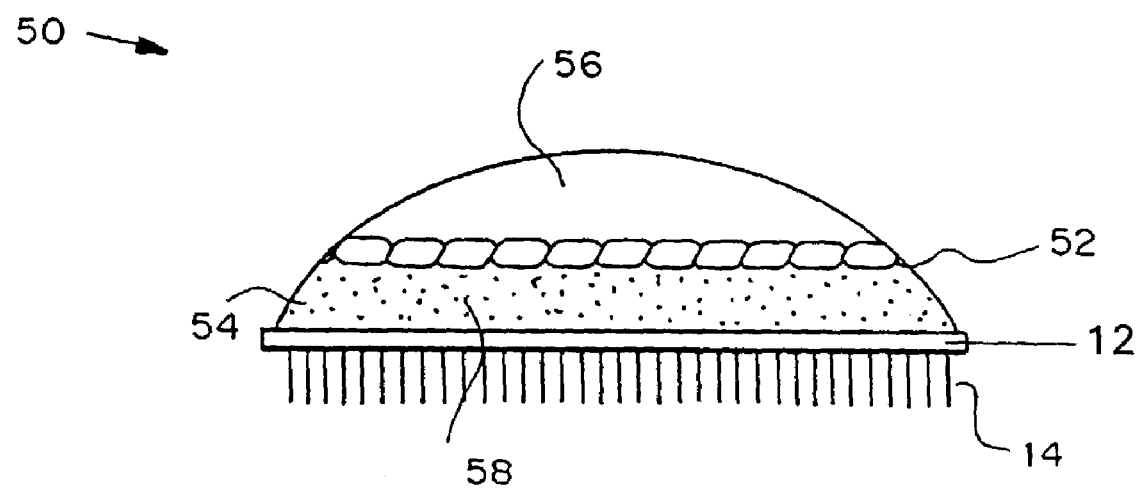

The reservoir of a single microneedle device can include a plurality of compartments that are isolated from one another and/or from a portion of the microneedles in an array. The device can, for example, be provided to deliver different drugs through different needles, or to deliver the same or different drugs at different rates or at different times (FIG. 4a). Alternatively, the contents of the different compartments can be combined with one another, for example, by piercing, or otherwise removing, a barrier between the compartments, so as to allow the materials to mix. In a preferred embodiment, one compartment contains a saline solution or another delivery vehicle, while another compartment contains lyophilized drug (FIG. 4b). In a preferred embodiment, the reservoir is a standard or Luer-Lock syringe adapted to connect to a microneedle array.

Methods for Manufacture of the Devices

The microneedle and substrate are made by methods known to those skilled in the art. Examples include microfabrication processes, by creating small mechanical structures in silicon, metal, polymer, and other materials. Three-dimensional arrays of hollow microneedles can be fabricated, for example, using combinations of dry etching processes; micromold creation in lithographically-defined polymers and selective sidewall electroplating; or direct micromolding techniques using epoxy mold transfers. These methods are described, for example, in U.S. Ser. No. 09/095,221, filed Jun. 10, 1998; U.S. Ser. No. 09/316,229, filed May 21, 1999; Henry, et al., "Micromachined Needles for the Transdermal Delivery of Drugs," *Micro Electro Mechanical Systems*, Heidelberg, Germany, pp. 494–98 (Jan. 26–29, 1998).

EXAMPLES

Figure 1B:
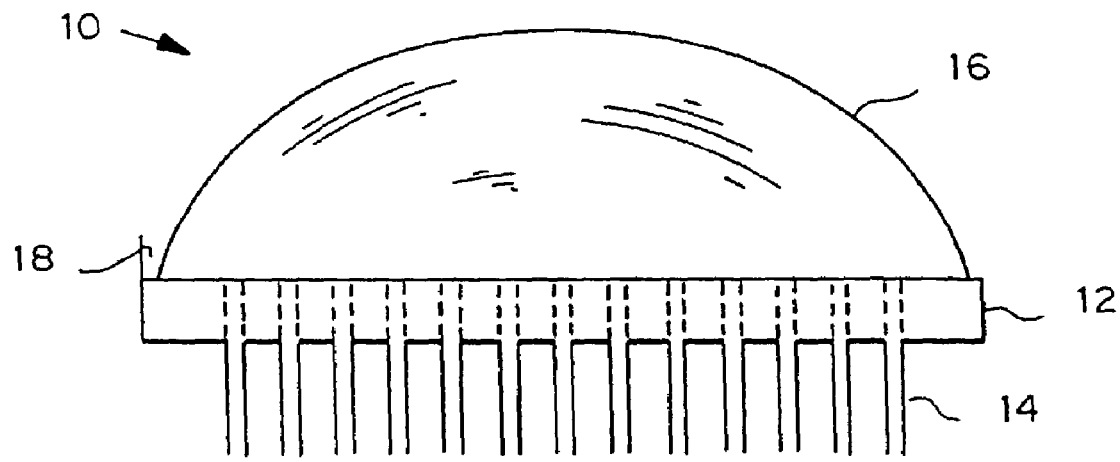
Figure 1C:
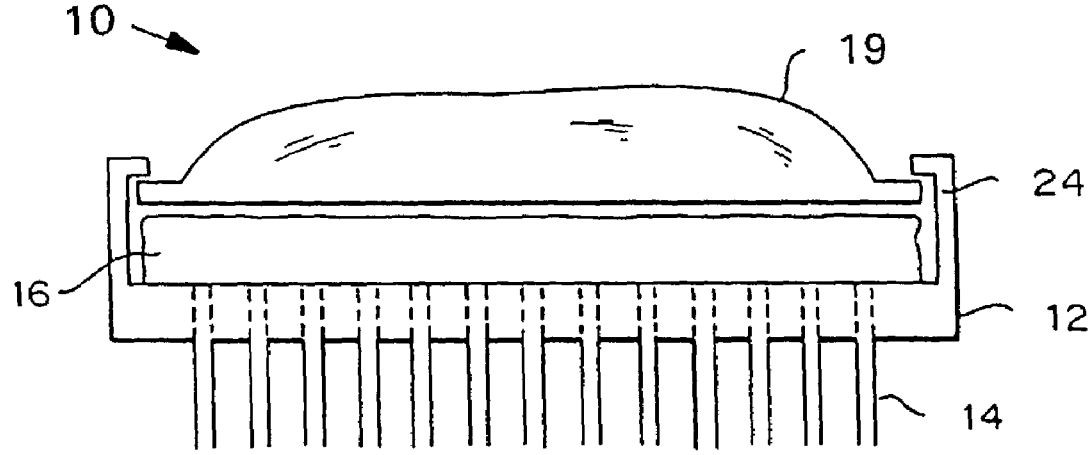

Preferred embodiments of the microneedle device are shown in FIGS. 1a–c. The device 10 includes substrate 12 from which a three-dimensional array of microneedles 14 protrude. As shown, the annular bore of the microneedles 14 extends through the substrate 12. The device 10 also includes a reservoir 16 secured to substrate 12 via a sealing mechanism 18. FIG. 1a shows how the reservoir can be accessed directly by application to the skin, for example, for simple transdermal delivery of an agent. The device in FIG. 1b includes a deformable bubble reservoir 16. Manual pressure can be used to expel its contents at the site of application. FIG. 1c shows a separate reservoir 16 from means 19 for expelling the contents of the reservoir 16 at the site of administration. The expelling means 19 can be simply a flexible bag. The expelling means 19 may also contain a vacuum so that it expands when vented, to create pressure on the reservoir, or it may be elastic so that it deforms when released from one position (not shown). Alternatively, reservoir 16 could be formed of an elastic material which deforms when released.

The sealing mechanism 18 can be, for example, an adhesive material or gasket. The sealing mechanism 18 can further function as or include a fracturable barrier or rate controlling membrane overlaying the surface of the substrate. In this embodiment, nothing can be released until a seal or peel-off strip covering is removed.

Figure 2:
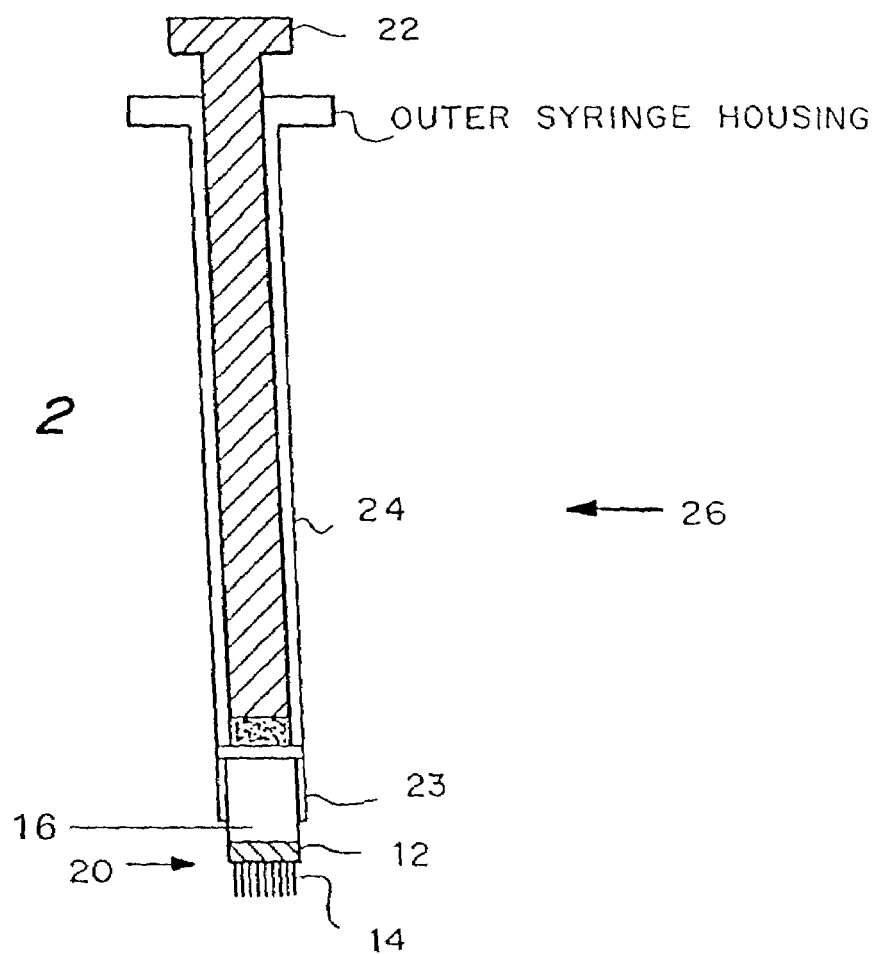
FIG. 2 is a cross-sectional view of another preferred embodiment of a microneedle drug delivery device, wherein delivery is activated by manual pressure applied via a plunger to compress the reservoir.

Another preferred embodiment of the microneedle device is shown in FIG. 2. The device 20 includes substrate 12 from which a three-dimensional array of microneedles 14 protrude. The device 20 also includes plunger 22 that is slidably secured to the upper surface of substrate 12 by plunger guide frame 24 using a restraint such as a Luer-lock interface 23. The substrate 12 can be attached or detached to a syringe 26 via a connector such as a Luer-lock type attachment 23. The plunger 22, guide frame 24, and connector 23 connect to, form or contain reservoir 16. A Luer-lock type attachment could alternatively be used to secure the device to means for controlling flow or transport through the device such as a pump.

Figure 3:
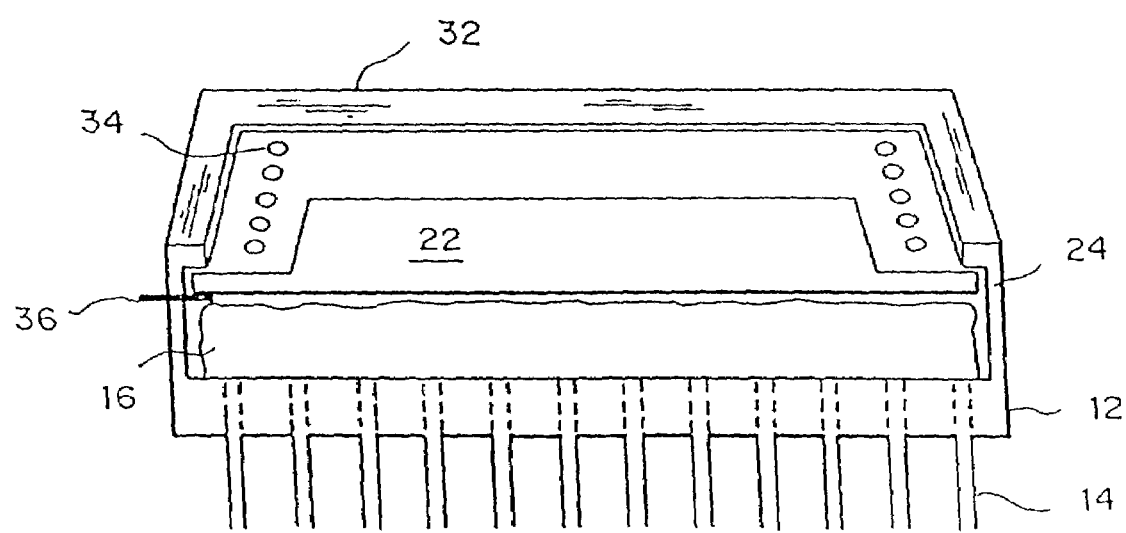
FIG. 3 is a cross-sectional view of another preferred embodiment of a microneedle drug delivery device, wherein delivery is activated by releasing a compressed spring which forces the plunger to compress the reservoir.

A further preferred embodiment of the microneedle device is shown in FIG. 3. Like the device in FIG. 2, the device 30 includes substrate 12, microneedles 14, plunger 22, plunger guide frame 24, and reservoir 16. Device 30 further includes plunger housing 32, which is attached to, or integrally formed with, plunger guide frame 24. A compressed spring or other tension-based mechanism 34 is positioned between plunger housing 32 and plunger 22. The device 30 further includes spring hold/release mechanism 36, which keeps the plunger up (spring compressed) until triggered to compress reservoir 16.

Attachment Feature

In a preferred embodiment, the microneedle device includes an adhesive material to secure the microneedle device to the skin, temporarily immobilizing the microneedles while inserted into the skin to deliver the drug. The adhesive agent typically is applied to the substrate (in between the microneedles at their base) or to an attachment collar or tabs adjacent the microneedles.

Care must be taken so that any adhesive agent does not plug the bores of hollow microneedles. For example, the adhesive agent can be applied in a liquid solution by flooding the top of the substrate below the tips of the microneedles, such as from the side of an array of microneedles, or by using a three-dimensional printing process. The solvent can then be evaporated from the adhesive agent solution, thereby precipitating or gelling the adhesive agent to yield a tacky surface. An alternate method of keeping the tips free of an applied adhesive agent is to choose materials of construction having a hydrophobicity or hydrophilicity to control the wetting of the surface to the microneedle tips.

Initiating Delivery

In a preferred embodiment, delivery of the drug from the reservoir is initiated by applying a force, such as by pressing the top of the reservoir, to cause the reservoir contents (i.e. a drug containing composition) to flow out through the microneedles—an active or dynamic process. For example, the user can apply finger-pressure directly to a deformable reservoir "bubble," (FIG. 1) or to a plunger mechanism (FIG. 2) or a Luer-lock type syringe that in turn causes the drug composition to be forced from the reservoir. The plunger also can be adapted to activate by application of a constant, reproducible force, for example, a spring (e.g., under compression) (FIG. 3) or elastic band (e.g., in tension).

A variation of this embodiment utilizes a balloon-like reservoir in tension to provide the force. Then, when an opening is formed in the balloon reservoir, the contents are forced out of the reservoir as the balloon contracts to its relaxed state. The contraction is selectively triggered to provide the driving force for delivery.

In a preferred embodiment, the force ruptures a fracturable barrier between the reservoir contents and the inlet of the microneedle. Representative barriers include thin foil, polymer, or laminant films. In another preferred embodiment, the microneedles tips are blocked until immediately before use. The blocking material can be, for example, a peelable adhesive or gel film, which will not clog the openings in the microneedle tip when the film is removed from the device.

Delivery also can be initiated by opening a mechanical gate or valve interposed between the reservoir outlet and the microneedle inlet. For example, a thin film or plate can be slid or peeled away from the back of the substrate.

In an alternate embodiment, delivery is initiated by changing the physical or chemical properties of the drug composition and/or of a barrier material. For example, the barrier can be a porous membrane having a porosity that can be selectably altered to permit flow, or the drug composition can be selected to change from a solid or semi-solid state to a fluid state, for example as the temperature is increased from ambient to that of body temperature. Such a drug composition can be prepared, for example, by combining the drug with a biodegradable polymeric material.

A preferred embodiment of the microneedle device is shown in FIG. 4a. FIG. 4a shows a device 40 in which microneedles 14 attached to a substrate 12 which is attached to multiple compartments 16a, 16b, 16c, and 16d. Each compartment can contain or function as a reservoir. Material can be expelled from each compartment through all or a subset of microneedles 14.

FIG. 4b depicts a device 50 in which microneedles 14 are attached to a substrate 12 which is attached to reservoir 58 containing, for example, lyophilized drug 54. The reservoir 58 is attached to a fracturable barrier 52 which is attached to another reservoir 56 containing, for example, saline. If the barrier 52 is fractured, then the two reservoirs 58 and 56 are in fluid communication with each other and their contents can mix.

Delivery also can be initiated by activating an osmotic pump, as described, for example, in U.S. Pat. No. 4,320,758 to Eckenhoff, which has been adapted to the substrate of the microneedle device. For example, the reservoir/osmotic pump includes an inner flexible bag that holds the drug charge, an intermediate layer of an osmotically effective solute composition, such as an inorganic salt, that encapsulates the bag, and an outer shape-retaining membrane that is at least in part permeable to water and that encapsulates both the layer of osmotically effective solute composition and the bag. In operation, the bag filled with the fluid drug compositions is exposed to an aqueous environment, so that water is imbibed from the environment by the osmotically effective solute through the membrane into the space between the inner flexible bag and the membrane. Since the bag is flexible and the membrane is rigid, the imbibed water squeezes the bag inwardly, thereby displacing drug out the microneedles.

Figure 5:
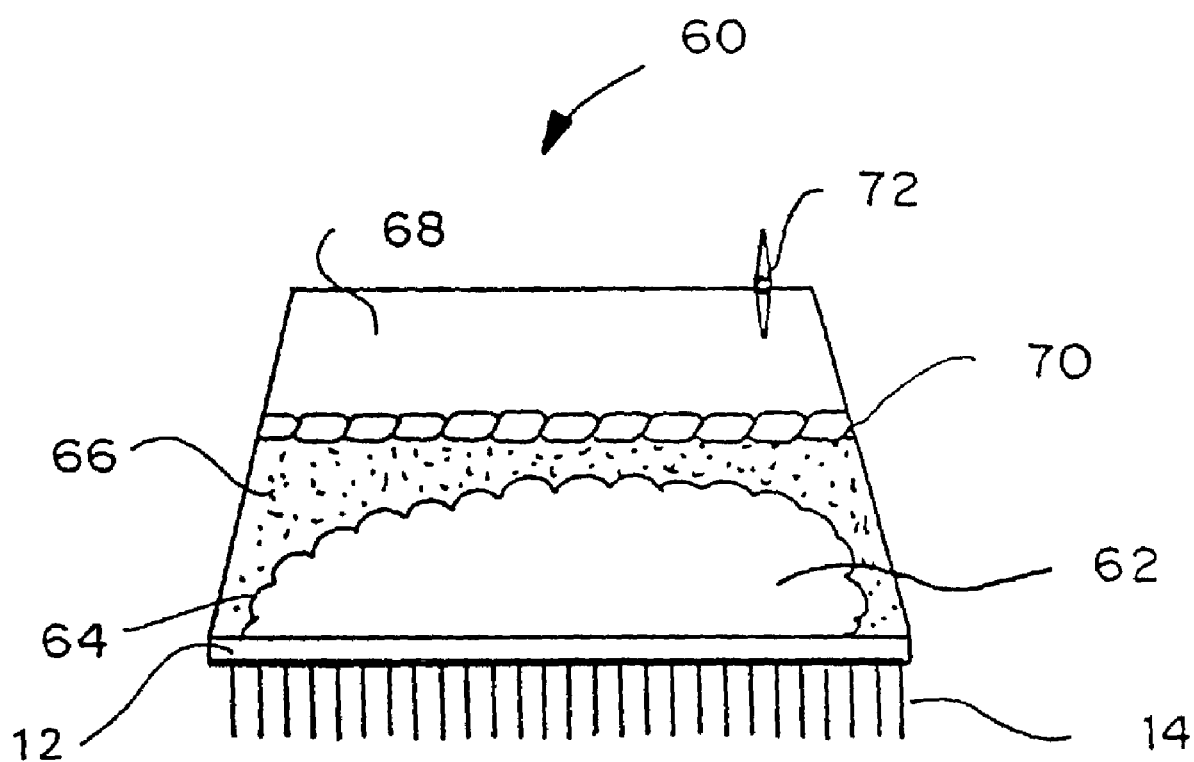
FIG. 5 is a cross-sectional view of a preferred embodiment of the microneedle drug delivery device, which incorporates an osmotic pump to force the drug contents from the reservoir.

FIG. 5 shows a device 60 in which microneedles 14 are attached to a substrate 12 which is attached to a drug reservoir 62. This reservoir is surrounded at least partially by a flexible, impermeable membrane 64. The drug reservoir is connected to another reservoir 66 which contains, for example, an inorganic salt. The two reservoirs 62 and 66 are separated by the impermeable membrane 64, which is impermeable to the contents of both reservoirs 62 and 66. The reservoir 66 is also connected to another reservoir 68 which contains, for example, an aqueous solution in which the organic salt is at least partially soluble. The two reservoirs 66 and 68 are separated by a rigid, semi-permeable membrane 70, which is partially or completely impermeable to the salt in reservoir 66 and partially or fully permeable to the solution in reservoir 68. There is also an optional fill port or vent 72 in communication with the reservoir 68, through which material can be added to or removed from the reservoir 68. Using this device 60, water can be drawn from the reservoir 68 across the semi-permeable membrane 70 into the reservoir 66 due to osmosis caused by the presence of salt in the reservoir 66. The flow of water will cause the volume of reservoir 66 to increase and thereby force the volume of reservoir 62 to decrease, which causes material to expel from reservoir 62 through microneedles 14.

In an alternate embodiment, delivery is initiated by opening the pathway between the reservoir and the microneedle tip, or unblocking the tip openings, and simply allowing the drug to be delivered by diffusion, that is, a passive process.

Feedback About Delivery

In a preferred embodiment, the microneedle device includes a feedback means so that the user can (1) determine whether delivery has been initiated; and/or (2) confirm that the reservoir has been emptied, that is delivery complete. Representative feedback means include a sound, a color (change) indicator, or a change in the shape of a deformable reservoir. In a preferred embodiment, the feedback for completion of delivery is simply that the reservoir is pressed flat against the back of the substrate and cannot be further deformed.

Feedback About Penetration of the Microneedles into the Tissue

The user of the microneedle device typically can Determine if the microneedles have been properly inserted into the skin or other tissue through visual or tactile means, that is assessing whether the substrate has been pressed essentially flush to the tissue surface. For example, if a puddle of liquid drug composition appears near the device, then the user may infer that the microneedles are not fully inserted, suggesting that the device needs to be reapplied. The liquid drug compositions can include a coloring agent to enhance the visual feedback.

In a more complex embodiment, an electrical or chemical measurement is adapted to provide the feedback. For example, penetration can be determined by measuring a change in electrical resistance at the skin or other tissue, or a pH change. Alternately, needle-to-needle electrical resistance can be measured. In a preferred embodiment, the microneedle device includes a disposable cartridge containing the microneedles. In these devices, an LED (e.g. green light/red light) or liquid crystal display can be provided with the reusable portion of the device.

Controlling the Delivery Rate

The microneedle device must be capable of transporting drug across or into the tissue at a useful rate. For example, the microneedle device must be capable of delivering drug at a rate sufficient to be therapeutically useful. The rate of delivery of the drug composition can be controlled by altering one or more of several design variables. For example, the amount of material flowing through the needles can be controlled by manipulating the effective hydrodynamic conductivity (the volumetric through-capacity) of a single device array, for example, by using more or fewer microneedles, by increasing or decreasing the number or diameter of the bores in the microneedles, or by filling at least some of the microneedle bores with a diffusion-limiting material. It is preferred, however, to simplify the manufacturing process by limiting the needle design to two or three "sizes" of microneedle arrays to accommodate, for example small, medium, and large volumetric flows, for which the delivery rate is controlled by other means.

Other means for controlling the rate of delivery include varying the driving force applied to the drug composition in the reservoir. For example, in passive diffusion systems, the concentration of drug in the reservoir can be increased to increase the rate of mass transfer. In active systems, for example, the pressure applied to the reservoir can be varied, such as by varying the spring constant or number of springs or elastic bands.

In either active or passive systems, the barrier material can be selected to provide a particular rate of diffusion for the drug molecules being delivered through the barrier at the needle inlet.

Drugs

Essentially any drug can be delivered using the microneedle devices described herein. As used herein, the term "drug" refers to an agent which possesses therapeutic, prophylactic, or diagnostic properties in vivo, for example when administered to an animal, including mammals, such as humans. Examples of suitable therapeutic and/or prophylactic active agents include proteins, such as hormones, antigens, and growth factors; nucleic acids, such as antisense molecules; and smaller molecules, such as antibiotics, steroids, decongestants, neuroactive agents, anesthetics, and sedatives. Examples of suitable diagnostic agents include radioactive isotopes and radioopaque agents, metals, gases, labels including chromatographic, fluorescent or enzymatic labels.

The drug can be or include a peptide, protein, carbohydrate (including monosaccharides, oligosaccharides, and polysaccharides), nucleoprotein, mucoprotein, lipoprotein, glycoprotein, nucleic acid molecules (including any form of DNA such as cDNA, RNA, or a fragment thereof, oligonucleotides, and genes), nucleotide, nucleoside, lipid, biologically active organic or inorganic molecules, or combination thereof.

The amount of drug can be selected by one of skill in the art, based, for example on the particular drug, the desired effect of the drug at the planned release levels, and the time span over which the drug should be released.

Multi-Cartridge Microneedle Device

A modification of the disposable, single use microneedle device utilizes a reusable triggering device (e.g., a plunger) in combination with a cartridge containing one or more, preferably a plurality, of single-use microneedle devices. For example, the cartridge can be a circular disk having 10 or 12 microneedle arrays connected to a single-dose reservoir, wherein the cartridge can be loaded into and unloaded from the triggering device. The triggering device can, for example, be designed to move a new dose into position for delivery, compress the reservoir to deliver the drug, and then eject or immobilize the used array. This type of reusable triggering device also can include a power source, such as a battery, used to operate a built-in measurement device, for example, for analyte measurement of interstitial fluids or electrical verification of needle penetration into skin, as described earlier in this document.

Microneedle Device Packaging

In a preferred embodiment following manufacture of the microneedle device, it is packaged for storage, shipment, and sale before use. The packaging should prevent contamination and damage. The packaging also should prevent premature triggering or release of any drug or vehicle contents from the reservoir.

It is particularly important that, the microneedle device is provided with a removable protective cover or cushion that protects the microneedles from damage. The protective cover also can function to keep the drug material from prematurely leaking out of the microneedles. In a preferred embodiment, an adhesive material or gel film used to selectively secure the cover over the microneedles. In an alternate embodiment, the film is antiseptic, and following removal can serve as a wipe to prepare the skin surface before insertion of the microneedles.

The packaging also can be adapted to serve as a vessel for safely disposing of the used microneedle device. In a preferred embodiment, the single-use microneedles are provided a device or material to shear the needles from the substrate or plug the microneedles, so as to prevent undesirable reuse of the device. In one embodiment, the inner back of the reservoir is provided with a tacky substance. When the reservoir is compressed against the back of the substrate following delivery of the reservoir contents, the tacky substance is driven into the opening of the microneedles, plugging them. In one embodiment of this device, the tacky material dries and hardens so that the substance cannot readily be removed.

Publications cited herein and the material for which they are cited are specifically incorporated by reference. Nothing herein is to be construed as an admission that the invention is not entitled to antedate such disclosure by virtue of prior invention.

Modifications and variations of the methods and devices described herein will be obvious to those skilled in the art from the foregoing detailed description. Such modifications and variations are intended to come within the scope of the appended claims.

We claim:

1. A method for delivering an agent into a biological barrier, comprising providing a device having:
   a plurality of hollow microneedles having a base end and a tip, with at least one hollow pathway disposed between the base end and the tip,
   a substrate to which the base ends of the microneedles are attached, and
   at least one reservoir containing the agent to be delivered and being in fluidic connection with the base ends of at least one of the microneedles,
   selectively altering the volume of the reservoir, and
   inserting at least one of the microneedles into the biological barrier to deliver an agent through the microneedles and into the biological barrier.

2. The method of claim 1 further comprising reducing the volume of the agent in the reservoir by driving the agent through at least one of the microneedles.

3. The method of claim 1 wherein the biological barrier is tissue.

4. The method of claim 1 further comprising providing a reservoir formed of a material which is deformable.

5. The method of claim 1 wherein the agent is selected from the group consisting of peptides, proteins, carbohydrates, nucleic acid molecules, lipids, organic molecules, biologically active inorganic molecules, and combinations thereof.

6. The method of claim 1 further comprising providing a plunger for compressing the reservoir.

7. The method of claim 1 further comprising employing an adhesive material for securing the device during delivery.

8. The method of claim 1 further comprising adapting the substrate for removably connecting to a standard or Luerlock syringe.

9. The method of claim 1 further comprising fracturing a barrier interposed between the reservoir and the substrate.

10. The method of claim 1 further comprising monitoring feedback to indicate that delivery has been initiated or completed.

11. The method of claim 1 further comprising mixing the agent with particles capable of blocking the hollow pathway and thereby preventing delivery of the agent.

12. The method of claim 1 further comprising providing an osmotic pump to move agent.

13. The method of claim 1 comprising providing multiple reservoirs.

14. The method of claim 13 wherein the reservoirs are in communication with each other.

15. The method of claim 13 wherein one or more reservoirs contain a solid formulation and one or more reservoirs contains a liquid carrier for the solid formulation.

16. The method of claim 1 further comprising regulating the rate at which the agent flows through the microneedles.

17. The method of claim 16 whereby regulating comprises disposing a membrane within the hollow pathway for controlling the rate at which the agent follows through the hollow pathway.

18. The method of claim 1 further comprising providing multiple microneedle arrays and means for accessing one or more arrays at a time.

* * * * *